United States Patent
Yokouchi

(10) Patent No.: US 10,867,410 B2
(45) Date of Patent: Dec. 15, 2020

(54) IMAGE PROCESSING APPARATUS AND ENDOSCOPIC SYSTEM

(71) Applicant: OLYMPUS CORPORATION, Tokyo (JP)

(72) Inventor: Masahito Yokouchi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 323 days.

(21) Appl. No.: 15/955,063

(22) Filed: Apr. 17, 2018

(65) Prior Publication Data
US 2018/0232911 A1 Aug. 16, 2018

Related U.S. Application Data

(63) Continuation of application No. PCT/JP2016/081267, filed on Oct. 21, 2016.

(30) Foreign Application Priority Data

Nov. 4, 2015 (JP) .................. 2015-216958

(51) Int. Cl.
*A61B 1/00* (2006.01)
*G06T 7/90* (2017.01)
(Continued)

(52) U.S. Cl.
CPC ............ *G06T 7/90* (2017.01); *A61B 1/00006* (2013.01); *A61B 1/00009* (2013.01); *A61B 1/04* (2013.01);
(Continued)

(58) Field of Classification Search
None
See application file for complete search history.

(56) References Cited

U.S. PATENT DOCUMENTS 6,293,911 B1 9/2001 Imaizumi et al.
6,422,994 B1 7/2002 Kaneko et al.
(Continued)

FOREIGN PATENT DOCUMENTS

JP H06-105803 A 4/1994
JP H06-245899 A 9/1994
(Continued)

OTHER PUBLICATIONS

US 6,692,429 B1, 02/2004, Imaizumi et al. (withdrawn)
(Continued)

*Primary Examiner* — Timothy J Neal
(74) *Attorney, Agent, or Firm* — Scully, Scott, Murphy & Presser, P.C.

(57) ABSTRACT

An image processing apparatus includes: a first gain calculation circuit configured to extract only color component of infrared light and multiply it by a gain of a predetermined multiplication factor; a first color adjustment circuit configured to perform output by allocating the color component of the infrared light into green component and blue component; a second gain calculation circuit configured to set gains of the green component and blue component to equivalent multiplication and multiply the color component of the infrared light by a gain of a multiplication factor smaller than the predetermined multiplication factor; a second color adjustment circuit configured to convert the color component of the infrared light into the green component and convert the green component into a red component; and a switching unit configured to perform a switching process of inputting a captured image to one of the first and the second gain calculation circuits.

2 Claims, 8 Drawing Sheets

(51) Int. Cl.
*A61B 1/04* (2006.01)
*A61B 1/05* (2006.01)
*A61B 1/06* (2006.01)
*A61B 5/00* (2006.01)
*G02B 23/24* (2006.01)
*G02B 27/14* (2006.01)

(52) U.S. Cl.
CPC ............ *A61B 1/043* (2013.01); *A61B 1/051* (2013.01); *A61B 1/0638* (2013.01); *A61B 1/0646* (2013.01); *A61B 1/0653* (2013.01); *A61B 5/0035* (2013.01); *A61B 5/0071* (2013.01); *A61B 5/0086* (2013.01); *A61B 2576/00* (2013.01); *G02B 23/2484* (2013.01); *G02B 27/141* (2013.01); *G06T 2207/10024* (2013.01); *G06T 2207/10048* (2013.01); *G06T 2207/10068* (2013.01); *G06T 2207/30096* (2013.01)

(56) References Cited

U.S. PATENT DOCUMENTS

| | | |
|---|---|---|
| 6,790,174 B2 | 9/2004 | Kaneko et al. |
| 6,960,165 B2 | 11/2005 | Ueno et al. |
| 7,172,553 B2 | 2/2007 | Ueno et al. |
| 7,179,222 B2 | 2/2007 | Imaizumi et al. |
| 7,204,803 B2 | 4/2007 | Ueno et al. |
| 7,226,412 B2 | 6/2007 | Ueno et al. |
| 7,658,710 B2 | 2/2010 | Ueno et al. |
| 9,715,727 B2 | 7/2017 | Mihalca et al. |
| 2006/0173358 A1 | 8/2006 | Xie |
| 2008/0111894 A1* | 5/2008 | Tanimoto ............... H04N 5/332 348/222.1 |
| 2012/0197077 A1 | 8/2012 | Kaku |
| 2014/0340497 A1* | 11/2014 | Shigeta ............. A61B 1/00009 348/68 |
| 2015/0238127 A1 | 8/2015 | Saito |
| 2017/0020377 A1 | 1/2017 | Takeuchi et al. |
| 2017/0202443 A1 | 7/2017 | Mihalca et al. |

FOREIGN PATENT DOCUMENTS

| | | |
|---|---|---|
| JP | H10-201707 A | 8/1998 |
| JP | H11-089789 A | 4/1999 |
| JP | 2001-178673 A | 7/2001 |
| JP | 2003-126015 A | 5/2003 |
| JP | 2007-125245 A | 5/2007 |
| JP | 2012-152414 A | 8/2012 |
| JP | 2015-509404 A | 3/2015 |
| JP | 2015-160013 A | 9/2015 |
| WO | WO 2015/156153 A1 | 10/2015 |

OTHER PUBLICATIONS

International Search Report dated Dec. 20, 2016 issued in PCT/JP2016/081267.
Japanese Notification of Reasons for Refusual dated Apr. 27, 2017 issued in JP 2017-504114.

\* cited by examiner

FIG.8
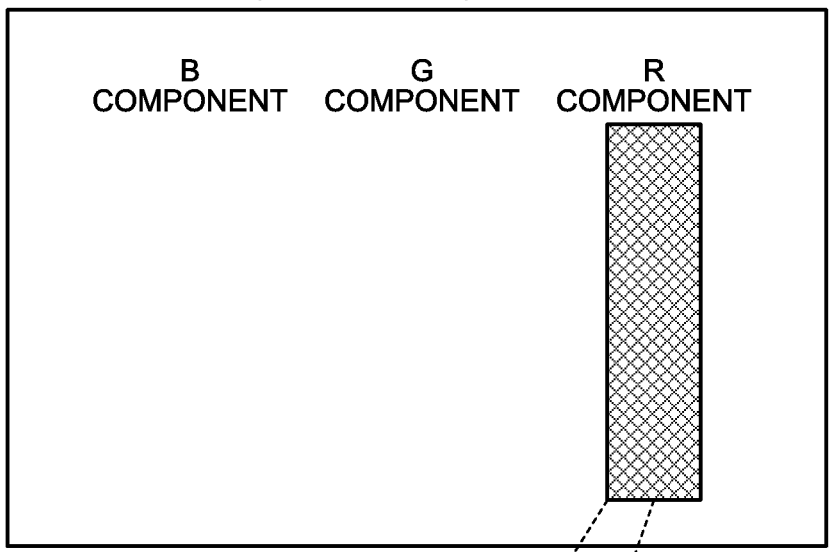
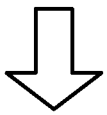
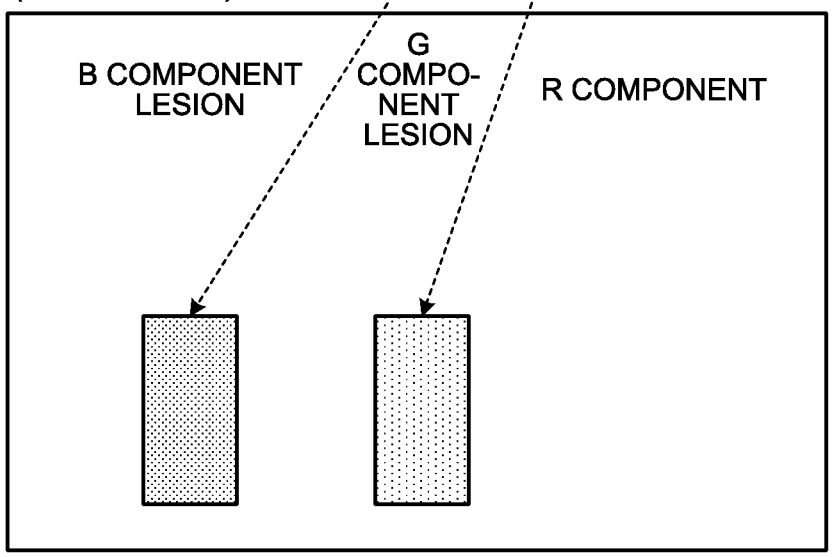

FIG.9
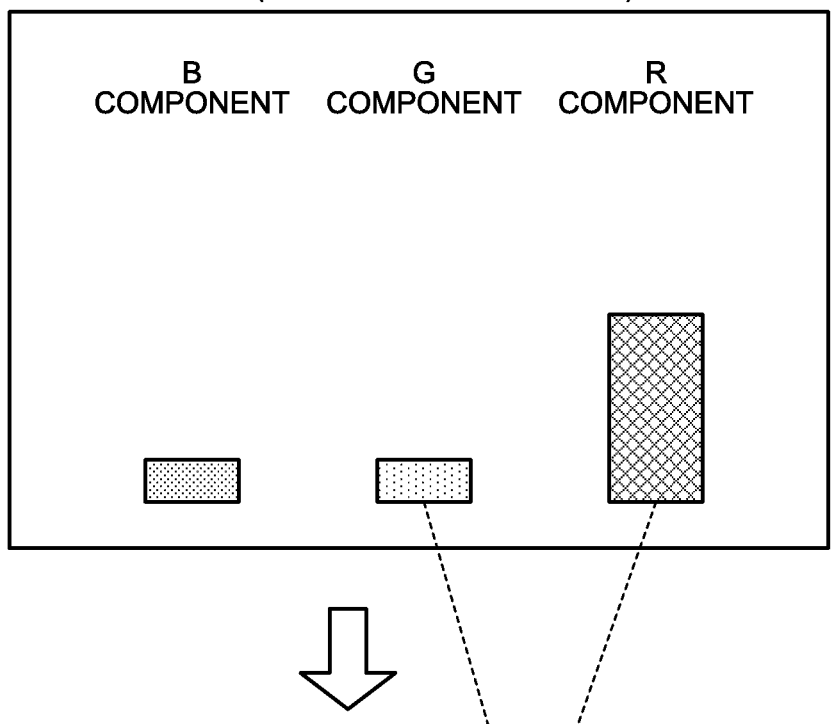
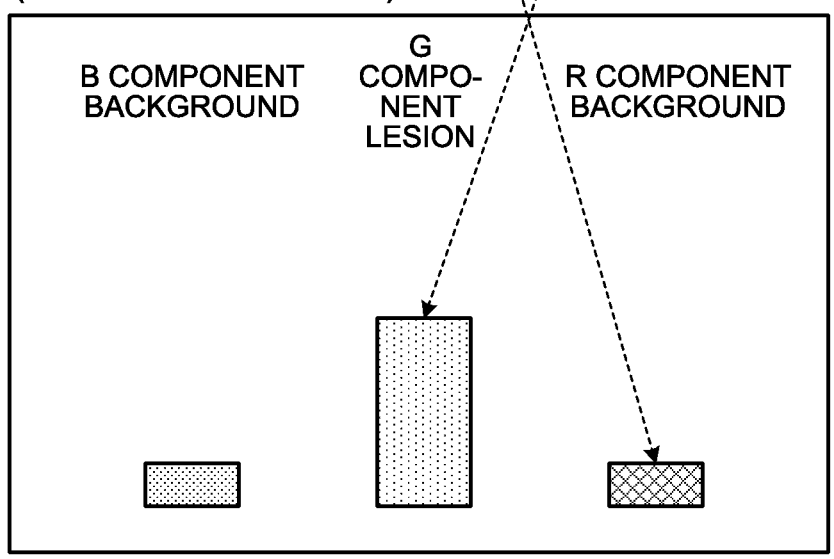

IMAGE PROCESSING APPARATUS AND ENDOSCOPIC SYSTEM

CROSS-REFERENCE TO RELATED APPLICATION

This application is a continuation of PCT International Application No. PCT/JP2016/081267 filed on Oct. 21, 2016, which claims the benefit of priority from Japanese Patent Application No. 2015-216958, filed on Nov. 4, 2015, the entire contents of which are incorporated herein by reference.

BACKGROUND

The present disclosure relates to an image processing apparatus and an endoscopic system.

In the related art, an endoscopic system that irradiates a lesion with excitation light and observes fluorescence from the lesion has been known. For example, JP 2015-509404 A discloses an image processing apparatus that displays a lesion emitting fluorescence and background other than the lesion in a highlighted manner with different colors in order to facilitate visibility at the time of performing a procedure for treatment on the lesion.

SUMMARY

In some embodiments, an image processing apparatus for performing predetermined processing on a captured image acquired by observation of special observation light, the captured image containing each color component of green, blue, and infrared light including fluorescent light emitted from a subject, includes: a first gain calculation circuit configured to extract only the color component of the infrared light out of the captured image and multiply the extracted color component of the infrared light by a gain of a predetermined multiplication factor; a first color adjustment circuit configured to perform output by allocating the color component of the infrared light output from the first gain calculation circuit into the green component and the blue component; a second gain calculation circuit configured to set gains of the green component and blue component to equivalent multiplication out of the captured image and multiply the color component of the infrared light by a gain of a multiplication factor smaller than the predetermined multiplication factor; a second color adjustment circuit configured to convert the color component of the infrared light output from the second gain calculation circuit into the green component and convert the green component into a red component; and a switching unit configured to perform a switching process of inputting the captured image to any one of the first gain calculation circuit and the second gain calculation circuit.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 8 is a view for describing a state of image processing in Color Mode 1;

FIG. 9 is a view for describing a state of image processing in Color Mode 2;

DETAILED DESCRIPTION

Figure 1:
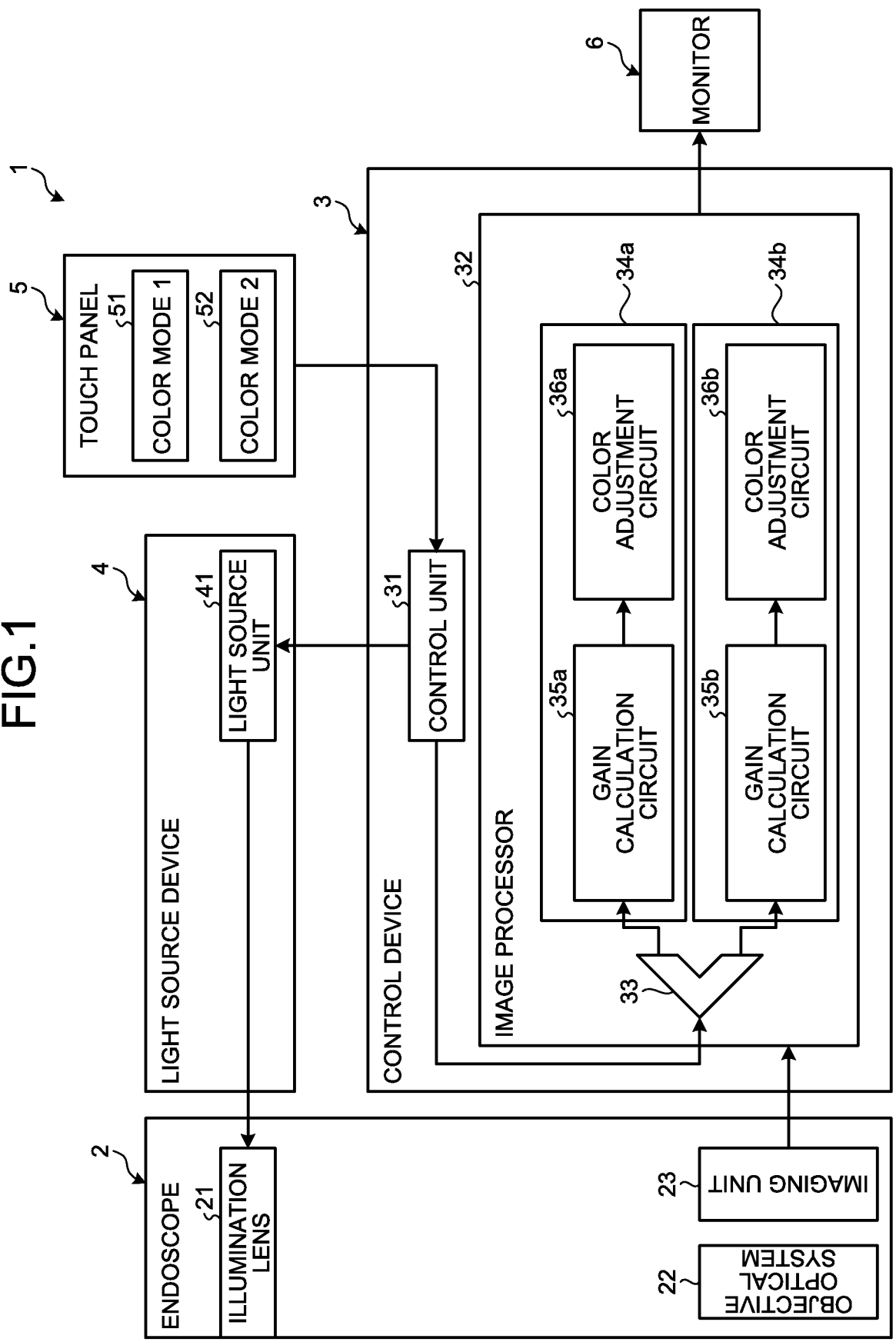
FIG. 1 is a schematic diagram illustrating a configuration of an endoscopic system including an image processing apparatus according to an embodiment.

Hereinafter, embodiments of an image processing apparatus, an endoscopic system, an image processing method, and an image processing program according to the present disclosure will be described with reference to the drawings. Note that the present disclosure is not limited to these embodiments. Although the following embodiments will be described by exemplifying the image processing apparatus for an endoscope, the endoscopic system, the image processing method, and the image processing program, the present disclosure may be generally applied to an image processing apparatus, an endoscopic system, an image processing method, and an image processing program for use in an apparatus that searches for a lesion and performs a procedure such as an endoscope and a microscope.

In addition, the same or corresponding elements are denoted by the same reference numerals as appropriate in the description of the drawings. In addition, it should be noted that the drawings are schematic, and a relation among dimensions of the respective elements, a ratio of the respective elements, and the like are different from the actual ones in some cases. The drawings may include some parts that have different dimensional relationships and ratios among the drawings in some cases.

Embodiment

FIG. 1 is a schematic diagram illustrating a configuration of an endoscopic system including an image processing apparatus according to an embodiment. As illustrated in FIG. 1, an endoscopic system 1 includes: an endoscope 2 serving as an imaging device which captures a captured image of a subject by inserting a distal end portion into a body cavity of the subject; a control device 3 which performs predetermined processing on the captured image captured by the endoscope 2 and integrally controls an operation of the entire endoscopic system 1; a light source device 4 which is a light source to generate illumination light or excitation light to be emitted from a distal end of the endoscope 2; a touch panel 5 through which an observer inputs a predetermined operation; and a monitor 6 which displays image data obtained by performing the image processing by the control device 3.

The endoscope 2 includes: an illumination lens 21 which is provided at the distal end of the endoscope 2 and outputs the illumination light or excitation light from the light source device 4; an objective optical system 22 for light collection; and an imaging unit 23 which is provided at an imaging position of the objective optical system 22 and receives light collected by the objective optical system 22, photoelectrically converts the received light into an electric signal, and outputs the electric signal as a captured image which has been subjected to predetermined signal processing.

The objective optical system 22 includes a lens that collects light inside the body cavity, a rigid endoscope filter that reflects excitation light pf a near-infrared region to be described later, and a color filter that transmits light of a predetermined wavelength band, and transmits the light of the predetermined wavelength band. The color filter is any one of an R color filter that transmits red (R) light and infrared light, a G color filter that transmits green (G) light, and a B color filter that transmits blue (B) light.

Figure 10:
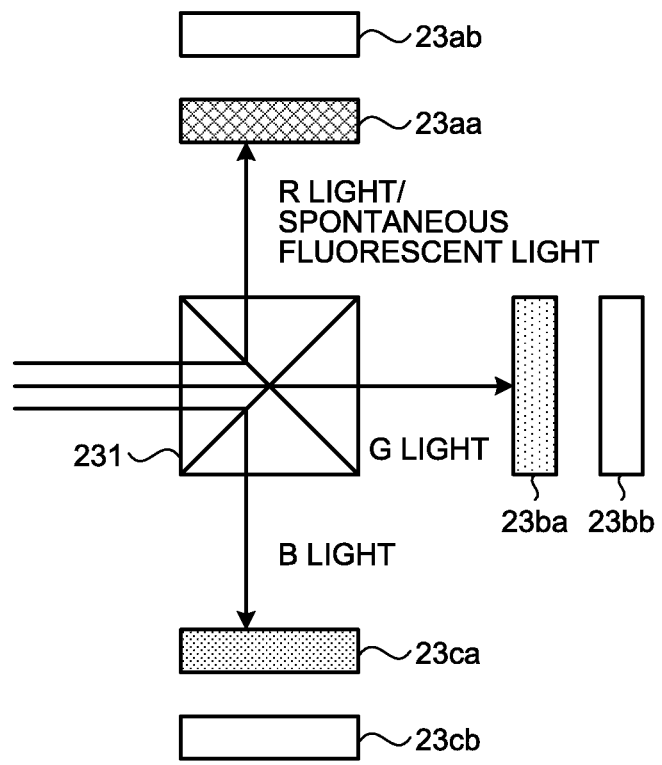
FIG. 10 is a view illustrating a configuration in which the imaging unit is realized using three types of image sensors and color filters.

The imaging unit 23 is configured using, for example, a charge coupled device (CCD) image sensor or a complementary metal oxide semiconductor (CMOS) image sensor. FIG. 10 is a view illustrating a configuration in which the imaging unit is realized using three types of image sensors and color filters. As illustrated in FIG. 10, light containing RGB components incident on the imaging unit 23 is divided by optical elements such as a prism 231 and enters each image sensor via each color filter. More specifically, the R light and infrared light enter an image sensor 23ab via an R color filter 23aa, the G light enters an image sensor 23bb via a G color filter 23ba, and the B light and infrared light are incident on an image sensor 23cb via a B color filter 23ca. The respective image sensors correspond to a plurality of pixels arranged in a two-dimensional lattice shape, and each pixel receives any one light among the R light, the G light, and the B light via each color filter, and photoelectrically converts the received light to generate the captured image.

The control device 3 includes a control unit 31 that controls the operation of the entire endoscopic system 1 and an image processor 32 serving as an image processing device that performs predetermined processing on the captured image captured by the endoscope 2.

The control unit 31 is configured using a CPU or the like, and performs driving control of each component and input and output control of information with respect to each component. The control unit 31 receives a signal input to the touch panel 5 and outputs a control signal corresponding to the input to the image processor 32.

The image processor 32 includes: a switching unit 33 that switches a color mode according to the signal from the control unit; a first color adjustment unit 34a that changes a color tone for a predetermined color component of the captured image; and a second color adjustment unit 34b that changes a color tone for the predetermined color component and another color component of the captured image. Further, the first color adjustment unit 34a includes a gain calculation circuit 35a that adjusts a gain for the predetermined color component and a color adjustment circuit 36a that converts the color tone for the predetermined color component. The second color adjustment unit 34b includes a gain calculation circuit 35b that adjusts gains for the predetermined color component and the other color component, and a color adjustment circuit 36b that converts the color tones for the predetermined color component and the other color component. The image processor 32 will be described in more detail later.

The light source device 4 includes a light source unit 41 that outputs illumination light or excitation light according to the control signal from the control unit 31. The light source unit 41 includes a white light emitting diode (LED) that outputs white illumination light and a special observation light source that outputs special observation light.

Figure 2:
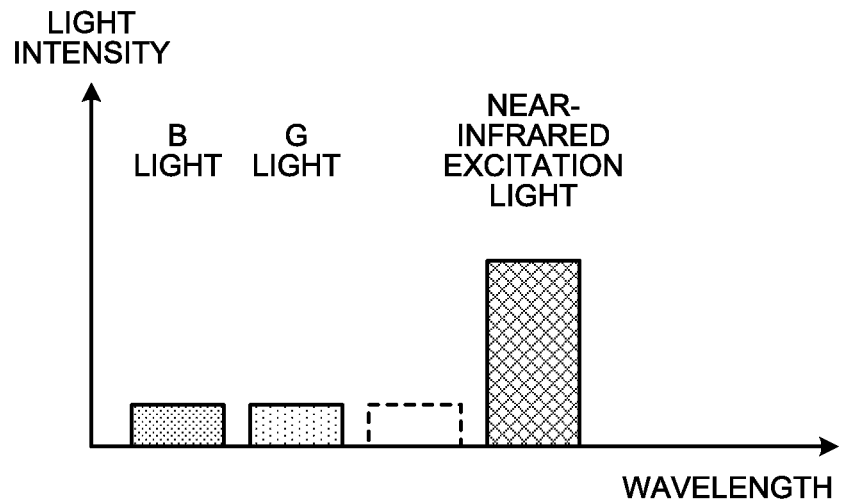
FIG. 2 is a diagram illustrating color components of special observation light output from a light source device.

FIG. 2 is a diagram illustrating color components of the special observation light output from the light source device. In FIG. 2, the vertical axis represents a light intensity and the horizontal axis represents a wavelength. As illustrated in FIG. 2, the special observation light source generates the excitation light of the near-infrared region to excite a fluorescent substance, which has been introduced into the subject and illumination light containing G light and B light to image the background. Therefore, the endoscopic system 1 has a function of performing observation with infrared Imaging (IRI). In addition, a light intensity of the excitation light of the near-infrared region is higher than light intensities of the G light and the B light. The special observation light generated by the special observation light source does not contain R light. Incidentally, for example, narrow band imaging (NBI) illumination light having two types of bands of G light and B light, narrowed so as to be easily absorbed by hemoglobin in the blood, or the like may be generated as the special observation light generated by the special observation light source.

The touch panel 5 includes a button 51 to switch the color mode to Color Mode 1 and a button 52 to switch the color mode to Color Mode 2. When the observer touches the button 51 or the button 52, a predetermined signal is output from the touch panel 5 and input to the control unit 31. Incidentally, the touch panel 5 may be replaced with a configuration that allows the observer to input a desired color mode, and may be replaced with, for example, a keyboard or a mouse.

The monitor 6 has a function of receiving the image data generated by the control device 3 via a video cable from the control device 3 and displaying the received image data. The monitor 6 includes a display such as liquid crystal or organic electro luminescence (EL) display.

Figure 3:
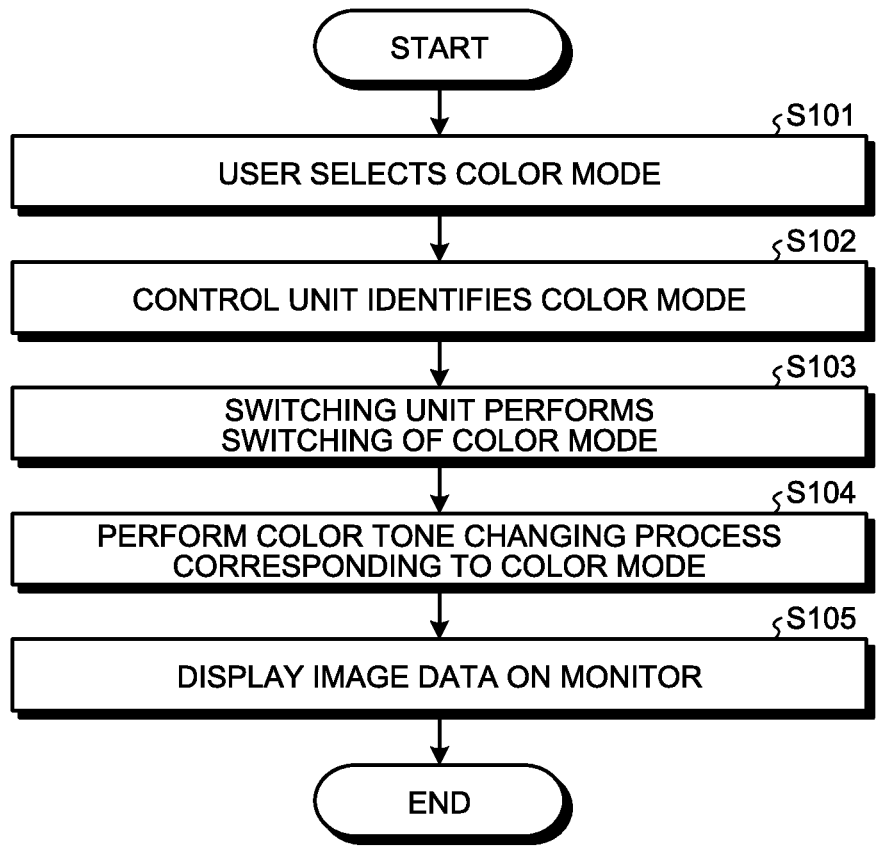
FIG. 3 is a flowchart illustrating an outline of processing executed by the endoscopic system according to the embodiment.

Next, processing at the time of observing the subject using the endoscopic system 1 will be described. FIG. 3 is a flowchart illustrating an outline of the processing executed by the endoscopic system according to the embodiment.

As illustrated in FIG. 3, the observer presses the button 51 or button 52 of the touch panel 5 to select Color Mode 1 or Color Mode 2 (a selection step: S101).

The input from the outside to the touch panel 5 is transmitted to the control unit 31 of the control device 3, and the control unit 31 identifies the color mode (an identification step: S102).

The control unit 31 outputs the control signal to the switching unit 33 of the image processor 32 so as to perform image processing corresponding to the identified color mode. The switching unit 33 of the image processor 32 switches Color Mode 1 or Color Mode 2 based on the control signal from the control unit 31 (a switching step: S103).

The image processor 32 performs a color tone changing process corresponding to Color Mode 1 or Color Mode 2 selected by the switching unit 33 with respect to the captured image including at least each of the red, green, and blue color components acquired by observation using the special observation light (a color tone changing step: S104).

The image processor 32 outputs the image data subjected to the image processing to the monitor 6. The monitor 6 displays the image data input from the image processor 32 (a display step: S105).

Here, the color tone changing processes performed in Color Mode 1 and Color Mode 2 by the image processor 32 will be described in detail. Color Mode 1 is a color mode to facilitate detection of a lesion when the observer searches for the lesion, and Color Mode 2 is a color mode to facilitate treatment when the observer performs the treatment on the lesion.

Figure 4:
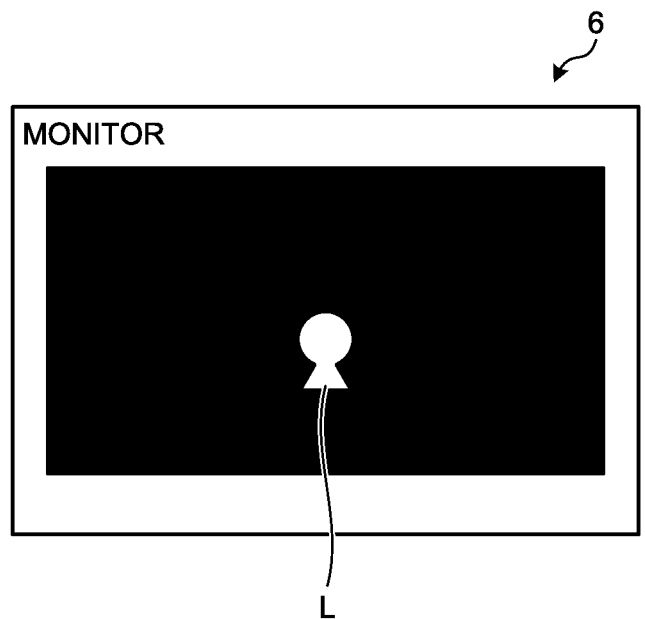
FIG. 4 is a view illustrating an example of an image displayed on a monitor when Color Mode 1 is selected.
Figure 5:
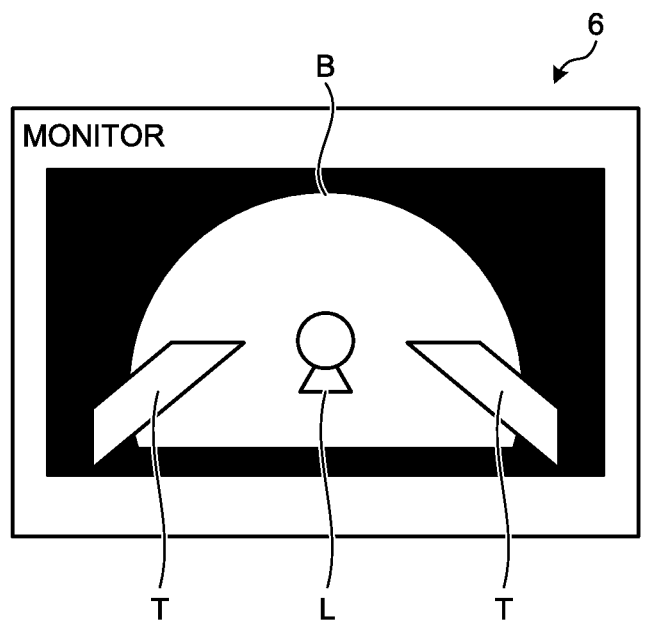
FIG. 5 is a view illustrating an example of an image displayed on the monitor when Color Mode 2 is selected.

FIG. 4 is a view illustrating an example of an image displayed on the monitor when Color Mode 1 is selected. FIG. 5 is a view illustrating an example of an image displayed on the monitor when Color Mode 2 is selected. In Color Mode 1, it is preferable that only a lesion L be displayed with a color tone which is easy to observe as illustrated in FIG. 4 in order to search for the lesion L. On the other hand, in Color Mode 2, it is preferable that both the lesion L and background B be displayed with color tones that are easy to observe as illustrated in FIG. 5. Incidentally, a treatment tool T is also displayed on the monitor 6 in FIG. 5.

First, a reagent in which the excitation light of the near-infrared region is easily absorbed is injected into the lesion L by injection or the like. Further, an observed region including the lesion L and the background B is irradiated with the special observation light having the color components of the light illustrated in FIG. 2. Then, the reagent absorbs the excitation light of the near-infrared region, and the subject emits spontaneous fluorescent light.

Figure 6:
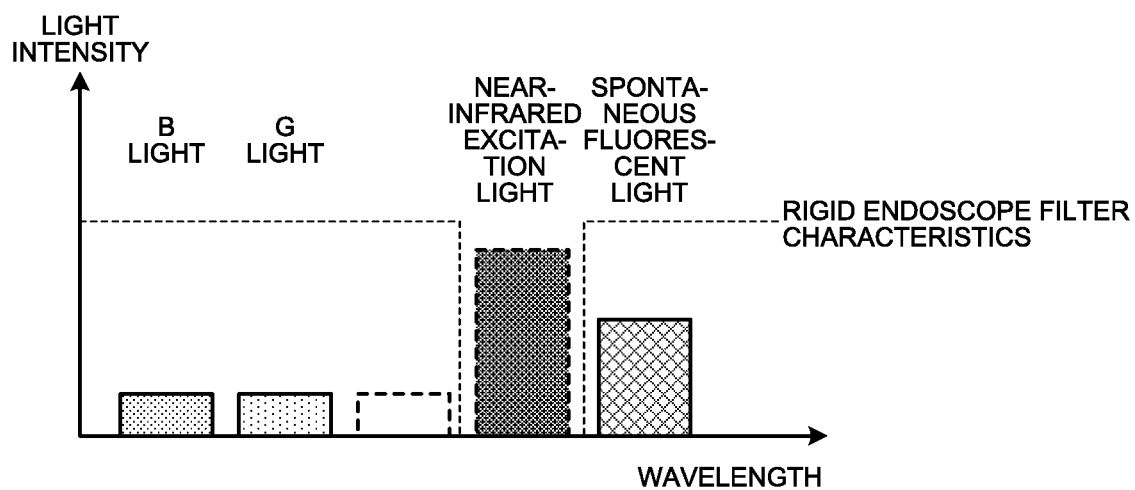
FIG. 6 is a diagram illustrating a light intensity of each color component of light incident on an endoscope.

FIG. 6 is a diagram illustrating a light intensity of each color component of light incident on the endoscope. In FIG. 6, the vertical axis represents a light intensity and the horizontal axis represents a wavelength. As illustrated in FIG. 6, the color components of the light incident on the endoscope 2 are color components of the excitation light of the near-infrared region directly reflected inside the body cavity of the subject, the B light, and the G light of the special observation light, and the spontaneous fluorescent light from the reagent in a near-infrared region having a longer wavelength than the excitation light. Here, the broken line in FIG. 6 indicates a wavelength band of light transmitted by the rigid endoscope filter of the objective optical system 22, and the rigid endoscope filter transmits the B light, the G light, and the spontaneous fluorescent light but does not transmit the excitation light of the near-infrared region.

Figure 7:
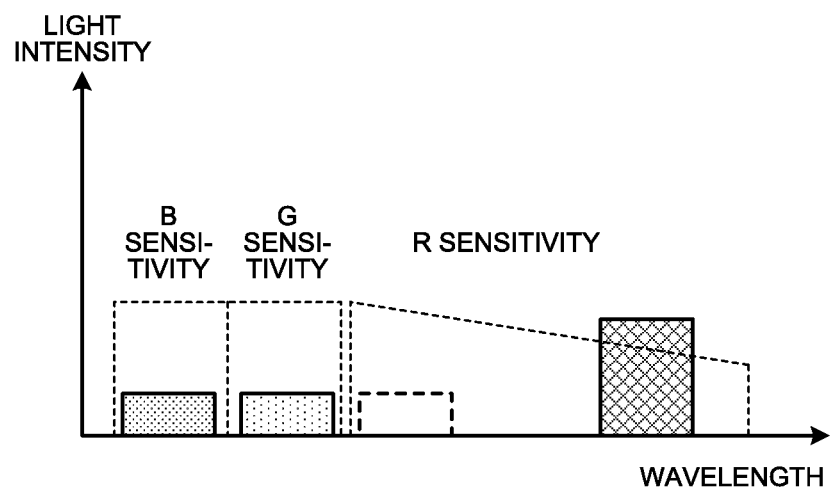
FIG. 7 is a diagram illustrating a light intensity of each color component of light detected by an imaging unit.

FIG. 7 is a diagram illustrating a light intensity of each color component of light detected by the imaging unit. In FIG. 7, the vertical axis represents a light intensity detected by the imaging unit 23, and the horizontal axis represents a wavelength. The broken line in FIG. 7 is a color component of light transmitted by each of the R, G, and B color filters. In other words, the broken line in FIG. 7 indicates the sensitivity of the imaging unit 23 with respect to each of the R, G, and B light. As illustrated in FIG. 7, the imaging unit 23 has sensitivity to the G light, the B light, the R light and the infrared light due to the color filters. In particular, the imaging unit 23 has sensitivity up to a region of spontaneous fluorescent light in an infrared region, and the color component of the infrared light is detected by the imaging unit 23 as an R component. The sensitivity in the infrared region is lowered on a longer wavelength side.

Light detected as the R component is the spontaneous fluorescent light from the reagent of the subject among the color components of the light detected by the imaging unit 23, and thus has information on the lesion L. On the other hand, light detected as G and B components among the color components of the light detected by the imaging unit 23 has information on the background B.

FIG. 8 is a view for describing a state of the image processing in Color Mode 1. When Color Mode 1 is selected, the gain calculation circuit 35a of the first color adjustment unit 34a performs a gain calculation process of extracting only the R component (that is, making gains of the G and B components to zero) and multiplying the extracted R component by a gain of k times in order to display only the lesion L. When this state is schematically illustrated, the color components of the light detected by the imaging unit 23 illustrated in FIG. 7 are converted into the color components illustrated in the upper view of FIG. 8.

Next, the color adjustment circuit 36a of the first color adjustment unit 34a performs a color adjustment process of allocating the R component to the G and B components as illustrated in FIG. 8. When this state is schematically illustrated, the color component illustrated in the upper view of FIG. 8 is converted into the color components illustrated in the lower view of FIG. 8. With this color adjustment process, even a slight difference in color tone of the lesion L may be made easily visible. Incidentally, the color adjustment process of evenly allocating the R component to the G and B components is illustrated in FIG. 8, but a color adjustment process of allocating the R component to the G and B components with weighting or allocating the R component to any one of the G and B components may be performed. Then, the image processor 32 outputs the image data subjected to the color adjustment process to the monitor 6, and the monitor 6 displays the image data. With the image processing that has been described as above, only the lesion L may be displayed as illustrated in FIG. 4.

FIG. 9 is a view for describing a state of the image processing in Color Mode 2. When Color Mode 2 is selected, the gain calculation circuit 35b of the second color adjustment unit 34b performs a gain calculation process of performing equivalent multiplication (directly using values without amplification) for gains of the G and B components and multiplying the R component by a gain of n times in order to display the lesion L and the background B. When this state is schematically illustrated, the color components of the light detected by the imaging unit 23 illustrated in FIG. 7 are converted into the color components illustrated in the upper view of FIG. 9.

Next, the color adjustment circuit 36b of the second color adjustment unit 34b performs a color adjustment process of converting the R component into the G component and the G component into the R component as illustrated in FIG. 9. When this state is schematically illustrated, the color components illustrated in the upper view of FIG. 9 are converted into the color components illustrated in the lower view of FIG. 9. With this color adjustment process, the lesion L may be displayed in a highlighted manner to be easily visible even with a slight difference in color, and the background B may also be made visible. Then, the image processor 32 outputs the image data subjected to the color adjustment process to the monitor 6, and the monitor 6 displays the image data. With the image processing that has been described as above, the lesion L and the background B may be displayed as illustrated in FIG. 5.

Incidentally, the gain multiplication factor n in the gain calculation circuit 35b of the second color adjustment unit 34b is set to a value smaller than the gain multiplication factor k in the gain calculation circuit 35a of the first color adjustment unit 34a. In the first color adjustment unit 34a, the color adjustment circuit 36a generates the G and B components using only the R component extracted from the gain calculation circuit 35a. Thus, it is necessary to increase information amount of the R component and allocate the R component to the G and B components, and thus, the gain multiplication factor k becomes a large value.

On the other hand, in the second color adjustment unit 34b, the color adjustment is performed using each information amount of the R, G, and B components, and thus, it is possible to generate the image with the gain multiplication factor n smaller than that of the first color adjustment unit 34a. When the gain calculation is performed, there are a disadvantage that noise component increases so that noise becomes conspicuous and a disadvantage that the information amount of the color component is clipped so that halation occurs. In order to reduce such influence, the gain multiplication factor n, which is smaller than the gain multiplication factor k of the first color adjustment unit 34a, is set in the second color adjustment unit 34b.

In the endoscopic system 1, it is possible to switch the image processing in the image processor 32 between Color Mode 1 in which only the lesion L is displayed in a highlighted manner and Color Mode 2 in which the lesion L and the background B are displayed based on the input of the observer. Therefore, the image processor 32 is the image processing device which generates the image data that is easy to observe in both the case of searching for the lesion and the case of applying treatment to the lesion.

Incidentally, a rigid endoscope having the rigid endoscope filter that reflects the excitation light of the near-infrared region of the special observation light has been described in the above-described embodiment, but the present disclosure is not limited thereto. The above-described image processing apparatus may be applied to a flexible endoscope having a flexible insertion portion to be inserted into the body cavity of the subject.

In addition, the configuration in which the switching unit 33 performs switching between Color Mode 1 and Color Mode 2 has been described in the above-described embodiment, but the present disclosure is not limited thereto. For example, the image processing apparatus may be configured such that both the first color adjustment unit 34a and the second color adjustment unit 34b constantly perform processing, and the monitor 6 displays the image data generated by the first color adjustment unit 34a and the image data generated by the second color adjustment unit 34b side by side. With this configuration, it is possible to simultaneously view an image in which only the lesion is highlighted by the first color adjustment unit 34a and an image in which the lesion and the background are displayed by the second color adjustment unit 34b.

In addition, the configuration in which switching is performed between the two color modes of Color Mode 1 and Color Mode 2 has been described in the above-described embodiment, but the number of color modes may be three or more.

In addition, the configuration in which the first color adjustment unit 34a includes the gain calculation circuit 35a and the color adjustment circuit 36a and the second color adjustment unit 34b includes the gain calculation circuit 35b and the color adjustment circuit 36b has been described in the above-described embodiment, the present disclosure is not limited thereto. For example, it may be configured such that the first color adjustment unit 34a includes an image processing circuit that collectively performs the gain calculation process and the color adjustment process on the captured image, and the second color adjustment unit 34b includes an image processing circuit that collectively performs the gain calculation process and the color adjustment process on the captured image. In this manner, the first color adjustment unit 34a and the second color adjustment unit 34b may be configured as one circuit, or may be configured with two or more circuits.

In addition, the adjustment of the gain for each color component in the first color adjustment unit 34a and the second color adjustment unit 34b of the image processing apparatus and the color adjustment process of each color component may be configured to be changed in accordance with a region to be observed. With this configuration, even when observing a plurality of regions with different colors, it is possible to generate image data that is easy to observe for each region.

Figure 11:
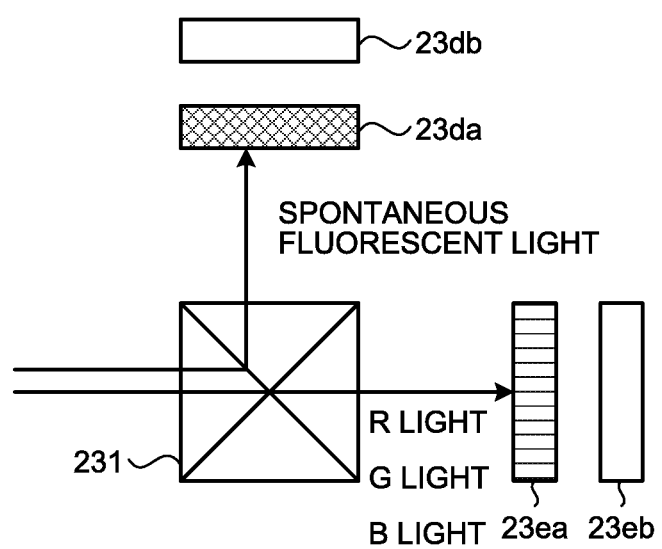
FIG. 11 is a view illustrating a configuration in which the imaging unit is realized using two types of image sensors and color filters.

In addition, the configuration in which the imaging unit 23 is realized by the three types of image sensors as illustrated in FIG. 10 has been described in the above-described embodiment, but it may be configured to include one image sensor with Bayer arrangement or configured as illustrated in FIG. 11 to include two types of image sensors of the image sensor for RGB and an image sensor to capture the spontaneous fluorescent light.

FIG. 11 is a view illustrating a configuration in which the imaging unit is realized using two types of image sensors and color filters. Specifically, the light incident on the imaging unit 23 is divided by an optical element such as the prism 231 into components of R light, G light, and B light and a component of spontaneous fluorescent light, light of the components of R light, G light, and B light enters a image sensor 23eb that receives the components of R light, G light, and B light via an RGB color filter 23ea, and light of the component of the spontaneous fluorescent light enters an image sensor 23db which receives the light of the component of spontaneous fluorescent light via an infrared color filter 23da.

Figure 12:
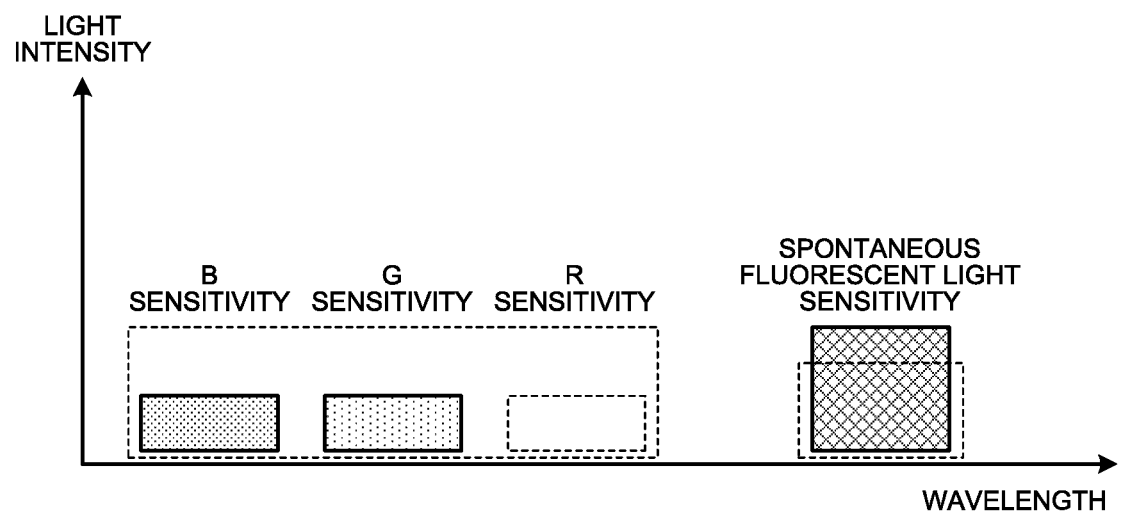
FIG. 12 is a diagram illustrating a light intensity of each color component of light detected by the imaging unit in the configuration of two types of image sensors.

FIG. 12 is a diagram illustrating a light intensity of each color component of light detected by the imaging unit in the configuration of the two types of image sensors illustrated in FIG. 11. Similarly to FIG. 7, the vertical axis represents a light intensity detected by the imaging unit 23, and the horizontal axis represents a wavelength. The broken line in FIG. 12 indicates a color component of the light transmitted by each color filter of the R light, G light, B light, and fluorescent component, in other words, sensitivity of the imaging unit 23 with respect to the R light, G light, B light, and spontaneous fluorescent light. With this configuration, the number of image sensors may be reduced, the structure of the imaging unit 23 may be decreased, and the endoscope 2 may be downsized.

According to the present disclosure, it is possible to realize an image processing apparatus, an endoscopic system, an image processing method, and an image processing program which generate image data that is easy to observe in both the case of searching for a lesion and the case of applying treatment to the lesion.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for performing predetermined processing on a captured image acquired by observation of special observation light that is excitation light of a near-infrared region and illumination light containing green light and blue light, the captured image containing each color component of green, blue, and infrared light including fluorescent light emitted from a subject, the image processing apparatus comprising:

a processor comprising hardware, wherein the processor is configured to:
        perform a first processing comprising:
            extract only the color component of the infrared light out of the captured image and multiply the color component of the infrared light extracted by a gain of a predetermined multiplication factor; and
            allocate the color component of the infrared light extracted and multiplied by the gain of the predetermined multiplication factor into the green component and the blue component output to a display;
        perform a second processing comprising:
            directly output, without amplification, the green component and blue component of the captured image and multiply the color component of the infrared light by a gain of a multiplication factor smaller than the predetermined multiplication factor; and
            convert the color component of the infrared light multiplied by the gain of the multiplication factor smaller than the predetermined multiplication factor into the green component and convert the green component directly output without amplification into a red component; and
        controllably switch between performing the first processing and performing the second processing.

2. An endoscopic system comprising:
the image processing apparatus according to claim 1;
a light source device configured to irradiate a subject with the special observation light; and
an endoscope including:
    a filter configured to reflect excitation light of a near-infrared region;
    a color filter, which is any one of a red color filter that transmits red light and infrared light, a green color filter that transmits green light, and a blue color filter that transmits blue light; and
    an image sensor including a plurality of pixels arrayed in a two-dimensional lattice shape and in which each of the pixels photoelectrically converts light received via the color filter to generate the captured image.

* * * * *